United States Patent [19]

Stone et al.

[11] Patent Number: 5,893,712

[45] Date of Patent: Apr. 13, 1999

[54] GRIPPING HANDLE FOR DIAGNOSTIC INSTRUMENT

[75] Inventors: Michael C. Stone, Skaneateles; Jack L. Connelly, Jr., Camillus; Richard A. Tamburrino, Auburn; Roger W. Leseberg, Liverpool; Robert L. Vivenzio, Auburn, all of N.Y.

[73] Assignee: Welch Allyn, Inc., Skaneateles Falls, N.Y.

[21] Appl. No.: 08/796,866

[22] Filed: Feb. 6, 1997

[51] Int. Cl.⁶ .................. A61C 1/00; A61C 3/00
[52] U.S. Cl. .................. 433/29; 433/116; 600/121; 600/125
[58] Field of Search .............. 433/116, 29; 600/121, 600/122, 125

[56] References Cited

U.S. PATENT DOCUMENTS

| | | | |
|---|---|---|---|
| 4,693,871 | 9/1987 | Geller | 433/116 |
| 4,723,912 | 2/1988 | Nieusma | 433/116 |
| 4,757,381 | 7/1988 | Cooper et al. | |
| 4,810,194 | 3/1989 | Snedden | 433/116 X |
| 4,823,949 | 4/1989 | Bala | |
| 4,846,334 | 7/1989 | Cargould | |
| 4,878,485 | 11/1989 | Adair | 600/125 X |
| 5,010,876 | 4/1991 | Henley et al. | 600/122 X |
| 5,069,337 | 12/1991 | Bala | |
| 5,107,988 | 4/1992 | Bala | |
| 5,154,164 | 10/1992 | Chikama | 600/125 X |
| 5,415,157 | 5/1995 | Welcome | 600/121 |
| 5,487,661 | 1/1996 | Peithman | |
| 5,490,781 | 2/1996 | Wade | 433/116 |
| 5,685,822 | 11/1997 | Harhen | 600/125 |

*Primary Examiner*—Nicholas D. Lucchesi
*Attorney, Agent, or Firm*—Wall Marjama Bilinski & Burr

[57] ABSTRACT

A diagnostic assembly includes an instrument having a body portion and a distal camera head, in which a protective sheath encases the instrument body and includes a transparent window for allowing the camera head to view a target. A releasably attached handle overlays the instrument body and includes inner surfaces conforming to the instrument body to clamp the sheath in a predetermined position to prevent the sheath and the transparent window form being twisted during use.

22 Claims, 3 Drawing Sheets

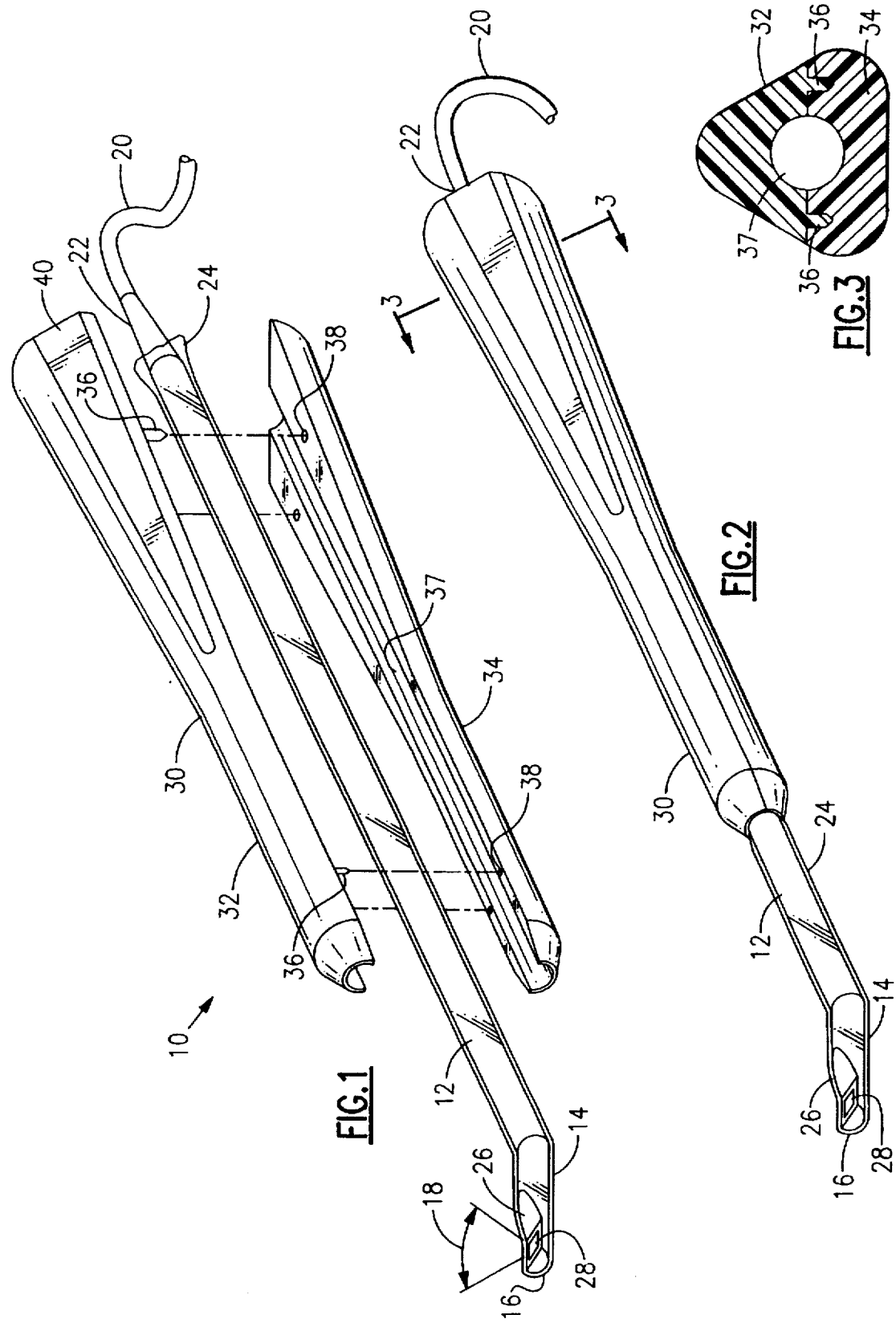

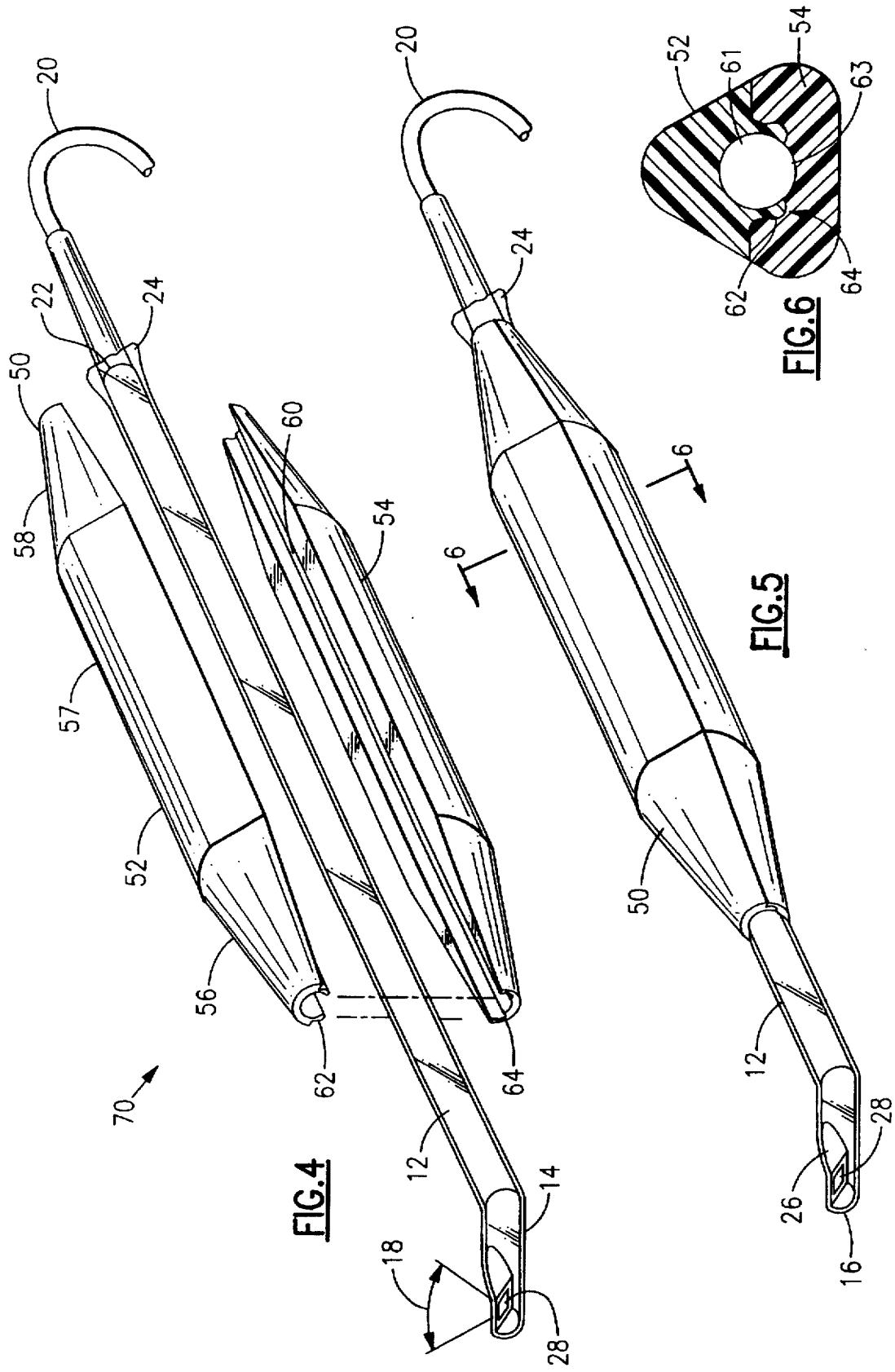

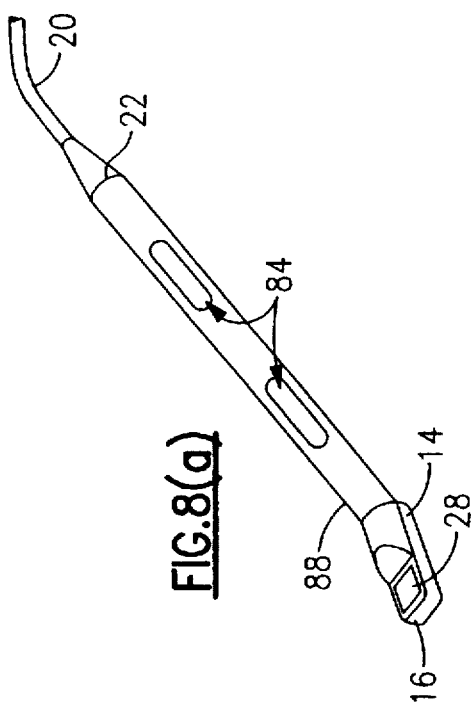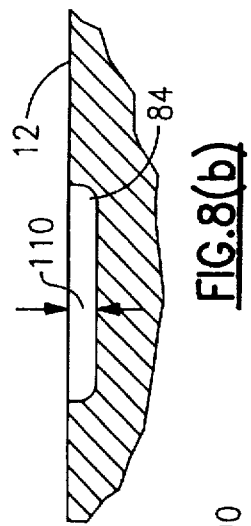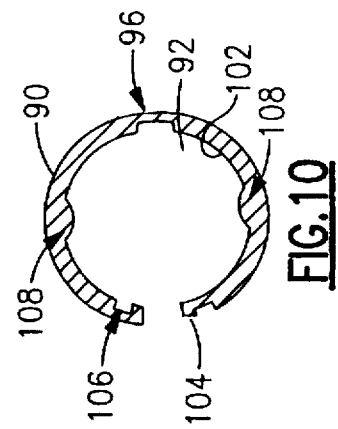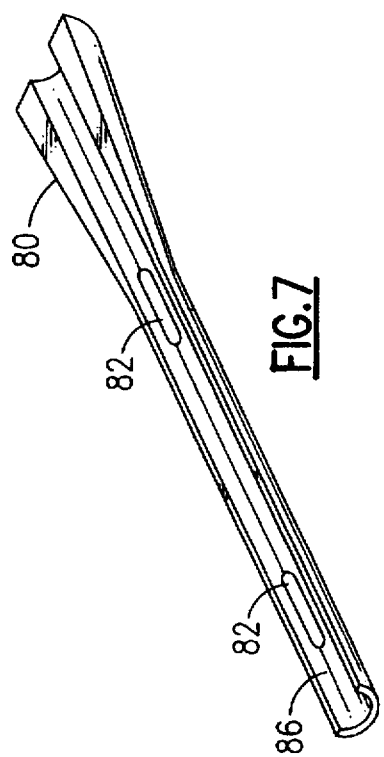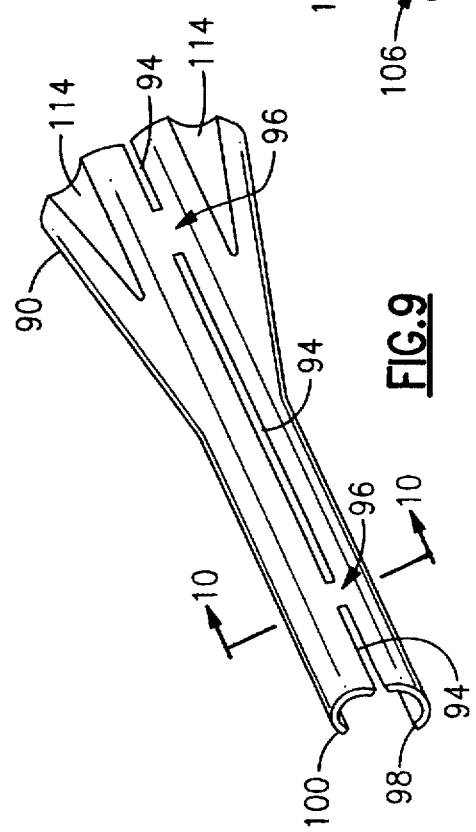

GRIPPING HANDLE FOR DIAGNOSTIC INSTRUMENT

FIELD OF THE INVENTION

This invention relates to diagnostic apparatus, and in particular to a gripping handle which is releasably attachable to the body portion of a diagnostic instrument.

BACKGROUND OF THE INVENTION

Diagnostic apparatus such as endoscopes, are conventionally known and used for medical purposes. Typically, an elongated tubular or other shaped instrument body includes a insertion portion having viewing optics contained therein for allowing inspection of a subject of interest.

Among such known devices are intraoral dental cameras having a micro-video camera retained within the distal head of an elongated instrument body sized for insertion into the mouth of a patient. The micro-video camera includes a viewing lens portion which focuses an optical image onto a solid-state imager, such as a CMOS or CCD. An electrical signal is then relayed to processing circuitry which converts the signal into a monitor-ready video signal further relayed to a video monitor or other processing apparatus for providing real-time diagnostic analysis.

There is a specific and urgent need to provide a clean and sterile camera surface to the patient for prudent medical reasons. This need is heightened because there is typically bleeding in even the most routine of dental procedures, by which transmission of Hepatitis B, AIDS, etc, might occur if the instrument is not properly handled between patients. Because of the design of the instrument, it is preferable that the camera head, as well as the tubular instrument body, be properly cleaned due to the proximity to the mouth of the patient.

Sterilization is an option in which the instrument is dipped in a liquid bath containing a sterilization agent. Application of heat using an oven or other specialized apparatus is still another option. Each of the above techniques among others, however, is time-consuming and may also affect the useful life of the instrument, which contains sensitive electronics and optics. Therefore, a protective flexible sheath, made from polyethylene or other suitable material, such as described in U.S. Pat. No. 4,757,381, has been developed which is sized to encase the tubular instrument body, including the distal camera head. The sheath includes a transparent viewing window to allow the lens portion of the camera to adequately view the subject area after the sheath has been applied.

In use, however, dentists or hygienists using the intraoral camera are required to grip the sheathed tubular instrument body in order to then inspect areas of a patient's mouth. Due to the loose fitting of the sheath to the instrument body, there are instances in which the sheath or the instrument is twisted, making support of the instrument difficult and invariably causing the viewing window of the sheath to be shifted from the field of view of the lens portion of the camera, producing unfavorable results.

The aforementioned '381 patent attempts to correct this problem in a number of ways, including heat shrinking a portion of the sheath to tighten the fit of the sheath onto the camera head. Alternative methods include applying a vacuum to the sheath or using fluid pressure to control the positioning of the sheath window in the vicinity of the camera lens. None of these methods are particularly convenient, nor do they aid in providing support for the user of the instrument.

The above stated problems are competing in a sense, in that use of a fixedly attached handle would ease in support of the instrument, but would not be acceptable for allowing easy removal and replacement of the protective sheath after each patient use.

Therefore, there is a need to provide an intraoral dental camera which uses the flexible protective sheath in a manner which allows easy attachment and removal of the sheath, but which allows the instrument to be supportable without twisting of the sheath member.

SUMMARY OF THE INVENTION

Therefore, according to a preferred aspect of the present invention, there is provided a diagnostic instrument assembly comprising:

an elongated instrument body; and a handle releasably attachable to said elongated instrument body, said handle defining a conforming cavity for fitting over the outer periphery of said elongated instrument body portion.

According to another preferred aspect of the present invention, there is provided a diagnostic camera assembly comprising:

an elongated instrument body having a distal camera head; and a flexible protective sheath for loosely covering at least a portion of said assembly, said sheath including a transparent window for allowing viewing access by said camera head, characterized by:

a handle releasably attachable to said elongated instrument body for clamping said sheath in a predetermined position, so as to prevent said window from being moved relative to said camera head during use.

Preferably, the handle is made from a biocompatible and flexible material formed either as a single bendable section, or as a pair of separate mating portions which, in either case, define a conforming cavity which allows fitting over an elongated instrument body.

According to another aspect of the present invention, there is provided a method of using a diagnostic medical instrument assembly including an elongated instrument body portion having a distal camera head and a flexible protective sheath for loosely covering said body portion and said head, said sheath having a transparent window for allowing viewing access to said camera head, comprising the steps of:

attaching the protective sheath to said intraoral camera assembly;

aligning the transparent window with the distal camera head; and attaching a releasably attachable handle to said instrument body portion, said handle defining a cavity for conforming to said instrument body wherein the handle clamps against said sheath to prevent the window from misaligning with the camera head when attached thereto.

An advantage in providing a handle as described is that the diagnostic camera can be reliably supported during use, despite the presence of the loose fitting protective sheath.

A further advantage of the present invention is that the handle can be easily and releasably attached to and removed from the diagnostic instrument, thereby allowing rapid reuse of the instrument without interfering with the removal of the protective sheath.

A further advantage of the present invention is that by providing a handle as described, the instrument can be used without fear of twisting the sheath, thereby allowing the camera to be used in a reliable manner.

These and other advantages, aspects, and features of the present invention are herein presented with reference to the following Detailed Description of the Preferred Embodiments and the following Drawings.

BRIEF DESCRIPTION OF THE DRAWINGS

FIG. 1 is an exploded perspective view of an intraoral dental camera assembly having a releasable handle made in accordance with a first embodiment of the present invention;

FIG. 2 is the perspective view of FIG. 1, illustrating the assembled intraoral dental camera assembly;

FIG. 3 is an enlarged partial view as taken in section along line 3—3 of FIG. 2;

FIG. 4 is an exploded perspective view of the intraoral camera assembly having a releasable handle made in accordance with a second embodiment;

FIG. 5 is the perspective view of FIG. 1 illustrating the assembled intraoral camera assembly of FIG. 4;

FIG. 6 is an enlarged sectional view as taken from line 6—6 of FIG. 5;

FIG. 7 is a partial perspective view of a releasable handle made in accordance with a third embodiment of the present invention;

FIG. 8(a) is a perspective view of an intraoral dental camera configured for use with the releasable handle of FIG. 7;

FIG. 8(b) is a partial sectional view of an alignment pocket of the camera of FIG. 8(a);

FIG. 9 is a perspective view of a releasable handle portion made in accordance with a fourth embodiment of the present invention; and FIG. 10 is a sectional view of the releasable handle portion of FIG. 9 as taken through line 10—10.

DETAILED DESCRIPTION OF THE PREFERRED EMBODIMENTS

The present invention is herein described with reference to certain preferred embodiments relating to an intraoral dental camera assembly. It will be readily apparent, however, that the description herein is suitable for other diagnostic apparatus, medical or otherwise.

A first embodiment is illustrated in FIGS. 1-3 of a intraoral dental camera assembly 10 including a tubular or cylindrically shaped instrument body member 12 having a head 14 located at a distal end 16 of the assembly. The head 14 is preferably angled relative to the remainder of the body 12 to allow a micro-video 95 camera disposed within the head 14 to define a field of view 18 through a lens portion 28. It should be noted that only the lens portion 28 has been illustrated, though cameras of the type herein described are known, such as described in U.S. Pat. No. 4,757,381, the entire contents of which are hereby incorporated by reference. A cable 20 extends from the proximal end 22 to transmit images from the micro-video camera to a video monitor (not shown) in a known manner. The details of the workings of the video camera and video processing apparatus are essentially known to those of ordinary skill in the art and do not necessarily form an essential part of the present invention. Therefore, a detailed discussion is not provided, except as required.

A protective sheath 24 is slipped over the distal end 16 of the instrument body member 12 as shown, covering the majority of the instrument. The sheath 24 is preferably made from a flexible rubber or plastic material, such as polyethylene or latex, and includes a viewing window 26 which serves to cover the lens portion 28 such that the sheath does not significantly impede the transmission of light to and from the camera head of the instrument. The viewing window 26 is typically made from a clear acrylic.

As noted, the sheath 24 loosely covers the instrument body 12 so that twisting of the sheath occurs as a result of varying finger pressure during actual use. Twisting of the sheath 24 can shift the position of the viewing window 26 and block the transmission of light from the lens portion 28 of the camera assembly 10.

The assembly 10, therefore according to the first embodiment, includes a split handle 30 including a pair of half sections 32, 34, each section being made of a molded biocompatible and recyclable plastic, such as Radel, or other suitable material, which is fitted over the outer periphery of the instrument body member 12 after the sheath 24 has been positioned as shown.

As particularly shown in FIGS. 1 and 3, each of the half sections 32, 34 of the split handle 30 defines, when assembled, an inner cavity 37 which is sized to conform to the outer periphery of the tubular instrument body member 12. A set of extending pins 36 are provided on the interior of one of the half sections 32 adjacent each end for engaging a corresponding set of holes 38 which are provided in the opposite half section 4. Preferably, each of the half portions 32, 34 also include gripping portions 40 for ease of use.

In operation, and prior to inserting the distal end 16 into the mouth of a patient (not shown), the protective sheath 24 is placed over the distal end 16 of the instrument body member 12 and the viewing window 26 is aligned with the lens portion 28 of the contained camera. The half portions 32, 34 of the split handle 30 are then fitted over a majority of the tubular instrument body member 12 by engagement of the mating pins and holes 36, 38, tightly retaining the tubular cross section within the inner cavity 37. The fitting of the split portions 32, 34 forms a sleeve which impinges upon the protective sheath 24, thereby restraining the sheath from twisting, while the gripping surfaces 40 provide additional support for a user.

When the oral examination of a patient's mouth is complete, the split handle 30 is disassembled from the instrument body member 12 by removing the pins 36 from the mating holes 38. The protective sheath 24 and the split handle 30 can then be removed and replaced. The handle portions 32, 34 can be discarded, or alternately be sterilized for reuse.

Referring now to FIGS. 4-6, a second embodiment of the present invention is herein described. For the sake of clarity, similar parts are labeled with the same reference numerals.

The second embodiment includes a dental camera assembly 70, including the instrument body member 12 of tubular or cylindrical cross-section having respective distal and proximal ends 16, 22.

According to this embodiment, a split handle 50, like that previously described, is defined by a pair of half sections 52, 54, each including a curved interior surface 61, 63, FIG. 6, defining an inner cavity 60 which conforms when assembled to the outer periphery of the tubular instrument body 12. One of the half sections 52 includes a pair of projecting longitudinal tabs 62 adjacent the curved interior surface 61 for engaging a corresponding interlock channel 64, FIG. 6, adjacent the curved interior surface 63 of the other half section 54. Preferably, and according to this embodiment, the sections 52, 54 each include opposite exterior tapered sections 56, 58 depending from a center portion 57 which allow ease of handling the instrument when the handle 50 is assembled thereto.

In operation, and as previously described above, the protective sheath 24 is slipped over the distal end 16 of the tubularly shaped instrument body member 12, such as also described in the previously incorporated U.S. Pat. No. 4,757,381. The half sections 52, 53, 54 are then positioned over the outer periphery of the tubular instrument body member 12 and attached together by aligning the longitudinal interlock tabs 62 within the corresponding interlock channels 64, thereby retaining the instrument body member 12 and attached sheath 24 within the inner cavity 60. The tapered sections 56, 58 aid in providing support, though it will be apparent that any convenient design can be utilized.

Upon completion of an oral examination, the handle 50 can be removed from the assembly 70 by either sliding one of the sections 52, 54 relative to the other, or by simply pulling the sections apart. The used protective sheath 24 can then be discarded, and the handle 50 either also discarded.

Referring now to FIGS. 7, 8(a) and 8(b), a third embodiment of a releasable handle will now be described according to the present invention. As in the preceding, those parts previously described will bear the identical reference numerals for the sake of clarity.

Referring first to FIG. 7, a half portion 80 of a releasable handle is illustrated, having a clamshell-like cross section similar to those portions 32, 34, FIG. 1, previously described in the first embodiment. For the sake of convenience, only one handle portion 80 is illustrated, having a inner cavity 86 which conforms so as to fit over the outer periphery of the instrument body 88 shown in FIG. 8(a). As in the preceding embodiments, the handle portion 88 is preferably made from a biocompatible and recyclable material, such as Radel, or other suitable material.

Furthermore, and referring briefly to FIG. 8(a), the instrument is similar to those previously described having a substantially tubular or cylindrical section and including distal and proximal ends 16, 22. A video camera (not shown) includes a lens portion 28 on an instrument head 14. A cable 20 extends from the proximal end 22 for engagement with a peripheral device such as a video monitor (not shown). Though not shown, a protective sheath 24, FIG. 1, fits over the instrument and includes a clear Viewing window 26, FIG. 1, which is aligned with the lens portion 28, also as previously described.

Referring back to FIG. 7, the handle portion 80 of this particular embodiment also includes a pair of molded-in and spaced protruding sections 82 which are sized to engage corresponding alignment pockets 84 provided on the instrument body portion 88, FIG. 8(a). Preferably, the alignment pockets 84 have a defined depth dimension 110 which allows seating of the protrusions 82 therein. In this manner, the split sections of the defined handle are not necessarily attached to each other, but are each independently attached to the instrument body 88. Though not shown, but for the sake of completeness, the instrument body 88 includes a second set of alignment pockets (not shown) for retaining alignment protrusions from a second handle portion (not shown).

In operation, the handle portion 80 is fitted over the camera body 88 after a protective sheath 24, FIG. 1, is applied over the instrument body as previously described. The alignment protrusions 82 of the handle portion 80 are aligned with the alignment pockets 84, to releasably attach the handle portion thereto and sandwiching the protective sheath 24, FIG. 1, therebetween. The remaining handle portion (not shown) is similarly attached to a corresponding set of alignment pockets (not shown) on the opposite side of the outer periphery of the instrument body 88. When an examination is completed, the handle portions are easily removed from the instrument body and the sheath can be discarded. The handle portions can either be sterilized, or discarded.

Referring to FIGS. 8(a)–10, a releasable handle according to a fourth embodiment will now be described. Rather than providing a pair of handle portions as described in the three preceding embodiments, the handle 90 according to this embodiment is made from a single piece of a bendable plastic or other suitable material. A series of longitudinal slots 94 are separated by a pair of hinge-like portions 96 which allows the handle 90 to be bent into a nearly circular cross section having a pair of ends 98, 100 which can be releasably attached together. According to this embodiment, one attachment end 98 of the handle 90 contains a tab 104 for engaging a slot 106 in the remaining attachment end 100 when the handle is fitted over the tubular instrument body 88. In addition, the interior surface 102 of the formed handle 90 includes a pair of alignment protrusions 108, similar to those previously described, and spaced to engage corresponding alignment pockets 84 provided on the outer periphery of the instrument body 88, FIG. 8(a).

It should be readily apparent that other variations or modifications of the described embodiments are possible to provide attachment and release of a handle to a diagnostic instrument, even those not requiring a protective sheath. For example, either of the handle portions of the first two embodiments can separately be attached to the instrument body as described in the third embodiment, or to each other, or both. In another example, the alignment pockets could be provided on the inner cavity of the handle portion for engaging protrusions on the outer periphery of the instrument body. In addition, other forms of releasable attachment can be imagined by one of sufficient skill in the field.

It should also be apparent that other configurations can be imagined in which the handle can be constructed to cover all or part of an instrument body member, wherein the instrument body can have different cross sections, in addition to the cylindrical or tubular configurations described herein.

PARTS LIST FOR FIGS. 1–10

10 dental camera assembly
12 instrument body
14 head
16 distal end
18 field of view
20 cable
22 proximal end
24 protective sheath
26 viewing window
28 lens portion
30 split handle
32 half section
34 half section
36 pins
38 holes
40 gripping portion
50 half section
52 half section
54 half section
56 tapered section 57 center section
58 tapered portion
60 cavity
61 inner curved surface
62 interlock tab
63 inner curved surface
64 interlock channel
70 dental camera assembly
80 handle portion
82 alignment protrusions
84 alignment pockets
86 cavity
88 camera body
90 handle section
92 cavity
94 slots
96 hingable portions
98 end
100 end
102 interior surface
104 tab
106 slot
108 alignment protrusions
110 depth dimension While this invention has been explained with reference to the structure disclosed herein, it is not confined to the details set forth and this application is intended to cover any modifications and changes within the scope of the following appended Claims.

What is claimed is:

1. An instrument assembly comprising:
   an elongated instrument body;
   a gripping handle portion releasably attachable to at least a portion of said elongated instrument body, said handle portion defining a conforming cavity sized for fitting over the outer periphery of said elongated instrument body;
   a camera head distally attached to said instrument body; and
   a flexible protective sheath for loosely covering at least a portion of said assembly including said distal camera head, said sheath including a transparent window for allowing viewing access by said camera head, said gripping handle portion covering a portion of said sheath wherein attachment of said gripping handle portion clamps said sheath in a predetermined position, so as to prevent said window from being moved relative to said camera head during use.

2. An assembly as recited in claim 1, wherein said gripping handle portion includes a pair of separable half portions forming an inner sleeve conforming to said elongated instrument body when said half portions are assembled thereto.

3. An assembly as recited in claim 2, wherein said half portions include means for releasably attaching to each other for securing said portions to said instrument body.

4. An assembly as recited in claim 1, wherein said gripping handle portion is a single section made from a flexible material which is bendable to form a conforming interior cavity sized to fit over the outer periphery of said instrument body, said section including a pair of mating section ends and means for releasably attaching said mating ends together to retain said handle portion to said instrument body.

5. An assembly as recited in claim 4, wherein said section includes a series of slots and at least one hingable portion to allow said section to form said conforming cavity.

6. An instrument assembly comprising:
   an elongated instrument body including a distally attached camera head;
   a flexible protective sheath for loosely covering at least a portion of said instrument body including said distal camera head, said sheath including at least one transparent window portion for allowing viewing access by said camera head; and
   a gripping handle portion releasably attachable to at least a portion of the outer periphery of said elongated instrument body for clamping said protective sheath in a predetermined position, so as to prevent said at least one transparent window portion from being moved relative to said camera head during use thereof.

7. An assembly as recited in claim 6, wherein said handle gripping handle portion includes a pair of separable half portions conforming to said instrument body forming an inner sleeve when said portions are assembled thereto.

8. An assembly as recited in claim 7, wherein said half portions include means for releasably attaching to each other for securing said portions to said instrument body.

9. An assembly as recited in claim 6, wherein said handle gripping handle portion is a single section made from a flexible material which is bendable to form a conforming interior cavity sized to fit over said instrument body, said section having a pair of section ends and means for releasably attaching said ends together to retain said handle to said instrument body.

10. An assembly as recited in claim 9, wherein said section includes a series of slots and at least one hingable portion to allow said section to form said conforming cavity.

11. An assembly recited in claim 6, wherein said handle gripping handle portion and said instrument body portion include releasable engagement means for allowing said handle gripping handle portion to be attached specifically to said instrument body.

12. An assembly as recited in claim 11, wherein said handle gripping handle portion includes at least one engagement portion protruding from said inner cavity for engaging said body, said body having means for receiving said at least one protrusion.

13. An assembly as recited in claim 12, wherein said handle gripping handle portion includes a plurality of protruding engagement portions for engaging a corresponding number of pockets formed on the outer periphery of said instrument body.

14. An assembly as recited in claim 6, wherein said assembly is an intraoral dental camera.

15. An assembly as recited in claim 6, wherein said handle gripping handle portion includes at least one gripping surface.

16. An assembly as recited in claim 6, wherein said handle gripping handle portion is disposable.

17. A method of using a medical instrument assembly, said assembly comprising an elongated instrument body, a camera head attached distally to said instrument body and a flexible protective sheath made from a thin material for loosely covering at least a portion of said body and said camera head, said sheath having a transparent window for allowing viewing access to said camera head, said method comprising the steps of:
   attaching the flexible, protective sheath to cover at least a portion of said instrument body and said camera head;
   aligning the transparent window with the distal camera head; and
   attaching a releasably attachable gripping handle portion to said instrument body, said gripping handle portion defining a cavity for conforming to the outer periphery of said instrument body so as to clamp over at least a portion of said sheath so as to prevent said window from being misaligned with the camera head.

18. A method according to claim 17, wherein said gripping handle portion includes a pair of releasably attachable mating sections, wherein the gripping handle portion attaching step includes the step of:

attaching a first mating section to said instrument body;

attaching a second mating section to said instrument body;

said method including the further step of removing said mating sections to allow said sheath to be removed from said assembly after use.

19. A method as recited in claim 17, wherein said gripping handle portion is a unitary bendable section having a pair of mating ends which when attached to each other define an interior cavity conforming to the outer periphery of said instrument body, said method comprising the steps of:

bending said unitary handle section over the outer periphery of said instrument body; and attaching one mating end of said handle portion to said remaining mating end, retaining said instrument body and said sheath there between.

20. An intraoral dental camera assembly comprising:

an elongated instrument body section including a distal camera head fixedly attached thereto;

a flexible protective sheath for loosely covering at least a portion of said body section, including said camera head; and a handle releasably attachable to said body section for clamping said protective sheath in a predetermined position so as to prevent twisting of said sheath during use.

21. An intraoral dental camera as recited in claim 20, wherein said handle includes a pair of separable half portions conforming to said elongated body and forming an inner sleeve when said portions are assembled thereto.

22. An intraoral dental camera as recited in claim 20, wherein said handle is a single section made from a flexible material which is bendable to form a conforming cavity sized to fit over said instrument body, said section having a pair of opposing ends and means for releasably attaching said ends together to retain said handle to said instrument body.

* * * * *